US011016098B2

(12) United States Patent
Kobold et al.

(10) Patent No.: US 11,016,098 B2
(45) Date of Patent: May 25, 2021

(54) METHOD FOR DETERMINING A CONCENTRATION OF A TARGET ANALYTE IN A SAMPLE OF BODILY FLUID

(71) Applicant: Roche Diagnostics Operations, Inc., Indianapolis, IN (US)

(72) Inventors: Uwe Kobold, Weilheim (DE); Roland Thiele, Kochel (DE); Noah Weiss, Cypress, TX (US); Benjamin Tiemann, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/158,931

(22) Filed: Oct. 12, 2018

(65) Prior Publication Data

US 2019/0049460 A1 Feb. 14, 2019

Related U.S. Application Data

(63) Continuation of application No. PCT/EP2017/058610, filed on Apr. 11, 2017.

(30) Foreign Application Priority Data

Apr. 14, 2016 (EP) .................................... 16165266

(51) Int. Cl.
*G01N 33/68* (2006.01)
*H01J 49/00* (2006.01)
(Continued)

(52) U.S. Cl.
CPC ......... *G01N 33/6848* (2013.01); *B01D 59/44* (2013.01); *G01N 30/72* (2013.01);
(Continued)

(58) Field of Classification Search
None
See application file for complete search history.

(56) References Cited

U.S. PATENT DOCUMENTS

2005/0023454 A1* 2/2005 Bateman ............. H01J 49/0036 250/288
2009/0088336 A1 4/2009 Burd et al.
(Continued)

FOREIGN PATENT DOCUMENTS

EP 2157432 A1 2/2010
EP 2662687 A4 11/2013
(Continued)

OTHER PUBLICATIONS

International Search Report dated May 29, 2017 in Application No. PCT/EP2017/058610, 6 pps.

*Primary Examiner* — James Choi
(74) *Attorney, Agent, or Firm* — Stinson LLP

(57) ABSTRACT

A method and an apparatus for determining a concentration of a target analyte in a sample of bodily fluid are disclosed. The method involves providing a sample of bodily fluid including the target analyte, providing an internal standard solution including a mixture of components having a plurality of isotopes of the target analyte, wherein a concentration of each isotope is unknown, adding the internal standard solution to the sample, analyzing the sample including the internal standard solution using a mass spectrometer, creating a sample function curve based on signal intensities, wherein the signal intensities define arbitrary units, transferring an analyte signal into a corresponding arbitrary analyte unit by means of the sample function curve, and transferring the arbitrary analyte unit into the concentration of a target analyte by means of a standardization function representing a curve of concentrations depending on the arbitrary units.

15 Claims, 5 Drawing Sheets

(51) Int. Cl.

| | |
|---|---|
| ***G01N 33/58*** | (2006.01) |
| ***G01N 33/96*** | (2006.01) |
| ***B01D 59/44*** | (2006.01) |
| ***G01N 30/72*** | (2006.01) |
| *G01N 1/28* | (2006.01) |

(52) U.S. Cl.

CPC ............. *G01N 33/58* (2013.01); *G01N 33/96* (2013.01); *H01J 49/0009* (2013.01); *G01N 2001/2893* (2013.01); *G01N 2458/15* (2013.01)

(56) References Cited

U.S. PATENT DOCUMENTS

| | | | | |
|---|---|---|---|---|
| 2011/0020942 | A1 | 1/2011 | Cerda et al. | |
| 2015/0198570 | A1 * | 7/2015 | Ozbal ................ | G01N 33/6848 250/282 |

FOREIGN PATENT DOCUMENTS

| | | | |
|---|---|---|---|
| JP | 2014-102102 | A | 6/2014 |
| WO | 2001/063284 | A2 | 8/2001 |
| WO | 2003/027682 | A2 | 4/2003 |
| WO | 2006/096704 | A2 | 9/2006 |
| WO | 2007/140291 | A2 | 12/2007 |
| WO | 2009/010764 | A1 | 1/2009 |
| WO | 2009/049189 | A1 | 4/2009 |
| WO | 2009/070233 | A1 | 6/2009 |
| WO | 2011/116028 | A1 | 9/2011 |
| WO | 2012/005838 | A1 | 1/2012 |
| WO | 2013/104004 | A1 | 7/2013 |
| WO | 2013/149963 | A1 | 10/2013 |
| WO | 2015/106169 | A1 | 7/2015 |

* cited by examiner

METHOD FOR DETERMINING A CONCENTRATION OF A TARGET ANALYTE IN A SAMPLE OF BODILY FLUID

CROSS REFERENCE TO RELATED APPLICATIONS

This application is a continuation of International Application No. PCT/EP2017/058610 filed Apr. 11, 2017, which claims priority to European Application No. 16165266.4 filed Apr. 14, 2016, the disclosures of which are hereby incorporated by reference in their entirety.

FIELD OF THE INVENTION

The disclosed method relates to a method for determining a concentration of a target analyte in a sample of bodily fluid.

BACKGROUND OF THE DESCRIPTION

In many biomedical and healthcare applications, the rapid determination of the concentration of an analyte in a bodily fluid such as blood, plasma, serum, urine, cerebrospinal fluid (CSF), or tissue extracts, is critically important. Traditionally, such measurements have been made via immunoassay-based techniques such as an enzyme linked immunosorbent assay (ELISA). Such techniques rely on the selective binding of an antibody to a target analyte within the sample. In most assays, a second antibody linked to a colorimetric, fluorometric, or radioactivity-based detection system is used to detect the analyte-antibody complex.

Many fully automated devices capable of running immunoassays on biological fluids have been developed and are commonly used in hospital and research settings. While these systems have the advantages of automation and capacity, they also have significant drawbacks. For example, the specificity and selectivity of each assay is only as good as the antibody being used.

More recently many of the quantitative assays in clinical and research settings traditionally analyzed by immunosorbent assays are being analyzed by mass spectrometry-based techniques.

Liquid or gas chromatography coupled to mass spectrometry (LC-MS or GC-MS) based methods are often considered the gold standard for absolute analyte quantitation measurements because of the inherent specificity, very good precision and high sensitivity. However, the quality of the absolute quantitation relies heavily on the quality of the calibration process used to convert measured signals into analyte concentrations. The state of the art methodology for LC-MS quantitation relies on the concept of stable isotope dilutions and an external calibration curve generated from reference standards.

The stable isotope dilution is a process where an isotopically labelled analyte structure (almost exclusively deuterated, $^{13}C$ labelled, $^{15}N$ labelled) is added to the sample as soon as possible in the sample preparation process. Hence, the sample is diluted with an isotope label. The isotope label is assumed or validated to have the identical properties as the target analyte in the sample, during the sample preparation and during the measurement process. Therefore, any random or systematic error in the process will affect the target analyte and isotope labelled analyte equally such that their concentration ratio will remain the same. An additional feature of the isotope labelled analyte is that it has a different mass (or more precisely mass to charge ratio) which allows it to be detected separately from the target analyte. Therefore, the process results in two independent signals, one from the target analyte ($S_A$) and one from the isotope labeled analyte ($S_{istd}$). The analyte signal is then normalized by the isotope labelled signal to produce a signal ratio, which is typically a peak area ratio, to adjust for any systematic or random errors which may have disturbed the process. This normalization process improves the overall precision The external calibration process relies on external calibrators containing known concentrations of target analyte which allow the mass spectrometry detector response to be described in the form of a calibration curve. Just like all samples to be tested, the calibrators are also spiked with the same amount of isotope labelled analyte. This allows the signal ratio response versus the analyte concentration to be plotted, the calibration curve.

Unknown samples spiked with isotope labeled analyte are measured to determine the signal ratio (signal analyte/signal isotope labelled analyte). This normalized signal response is then converted to concentrations using the externally generated calibration curve.

An external calibration curve, which relies on the principle of isotope dilution, is only valid when 1) the amount of isotope labelled analyte is exactly the same in the calibrators and all of the unknown samples to be quantified, 2) there is no difference in instrument response between the matrix of the calibrators and the matrix of the unknown samples to be measured and 3) the MS response at the time point of external calibration is the same as the MS response at the time point. Therefore, it is clear that the external calibration curve has a defined lifetime to which it is suitable to quantify unknown samples. This lifetime depends on how well controlled the three aspects above are. The risk is currently minimized be increasing the calibration frequency such that in many lab-developed LC-MS tests a new calibration curve is generated several times a day. Some methods demand a new full 7 point external calibration as often as every 20 unknown samples to ensure that the external calibration curve suitable for quantification is.

The strategy of increasing calibration frequency improves data quality and confidence while sacrificing measuring time. While this model is widely adapted in the clinical environment for batch modus assays, it is not very suited to handle a dynamic, multiplexing system capable of running many different assays in random access. The calibration demand in this case will be too high to allow for regular re-calibrations at this kind of daily frequency.

One approach to reduce the calibration frequency would be to shift to the concept of internal calibration, where the instrument response is described within each and every sample. This would have the potential to completely mitigate the need for external calibrators and costly external calibration time. In this case, stable isotope dilution procedure is the same, except that the isotope labelled analyte is signed the additional role as being a calibrator. This relies on assigning a concentration value to the isotope labelled analyte in order to convert analyte signals into analyte ratios. Differences in instrument response between the analyte and isotope labelled analyte are often included.

Significantly different in this case, is that the instrument response is defined by a surrogate analyte (isotope labelled analyte) and the validity of this process demands that the relative instrument response between the analyte and isotope labelled analyte is the same over time. If the MS response of the isotope labelled analyte should change relative to that of the signal response of the analyte, then the internal calibration response is no longer valid. Therefore, strategies to monitor and correct for changing isotope labelled analyte responses have also been described which rely on incorporating a response factor.

WO 2015/106169 A1 describes an internal calibration method using a single isotope labelled analyte as a single internal calibrator point.

Despite the advantages provided by an internal calibration method, the concept of a single point internal calibration has the following drawbacks: 1) the accuracy in an unknown sample depends on the reliability of a single calibration measurement, 2) the instrument response may not always be correctly described in the entire measuring range, 3) the problem of how to define a proper y-intercept (blank value) is not addressed, 4) quantification is not possible if the internal calibrator signal cannot be determined or if it is an outlier and 5) the precision is dependent on how closely the analyte and a single isotope labelled analyte track one another through the entire process.

SUMMARY OF THE INVENTION

All of these limitations can be solved by using more isotope labelled analytes in constructing the internal calibration. In the reality, this solution has its practical limitations because of the limited availability of different isotope labelled analytes. However, in at least one instance is the use of two independent isotope labelled analytes described for an internal calibration. Beyond this there are no further public descriptions of multi-point internal calibrations based on different isotope labelled analytes, to our knowledge. The synthesis of several differently isotope labelled analytes would be extremely costly and time consuming, for example $^{2}H_6$ and $^{13}C_3$ labelled analytes.

Disclosed herein is a method for determining a concentration of a target analyte in a sample of bodily fluid. Embodiments of the disclosed method for determining a concentration of a target analyte in a sample of bodily fluid have the features of the independent claim. Particular embodiments, which may be realized in an isolated way or in any arbitrary combination, are disclosed in the dependent claims.

BRIEF DESCRIPTION OF THE FIGURES

Further features and embodiments of the invention will be disclosed in more detail in the subsequent description of embodiments, preferably in conjunction with the dependent claims. Therein, the respective features may be realized in an isolated fashion as well as in any arbitrary feasible combination, as a skilled person will realize. The embodiments are schematically depicted in the figures. Therein, identical reference numbers in these figures refer to identical elements or functionally identical elements.

In the figures.

DETAILED DESCRIPTION OF THE INVENTION

Figure 1:
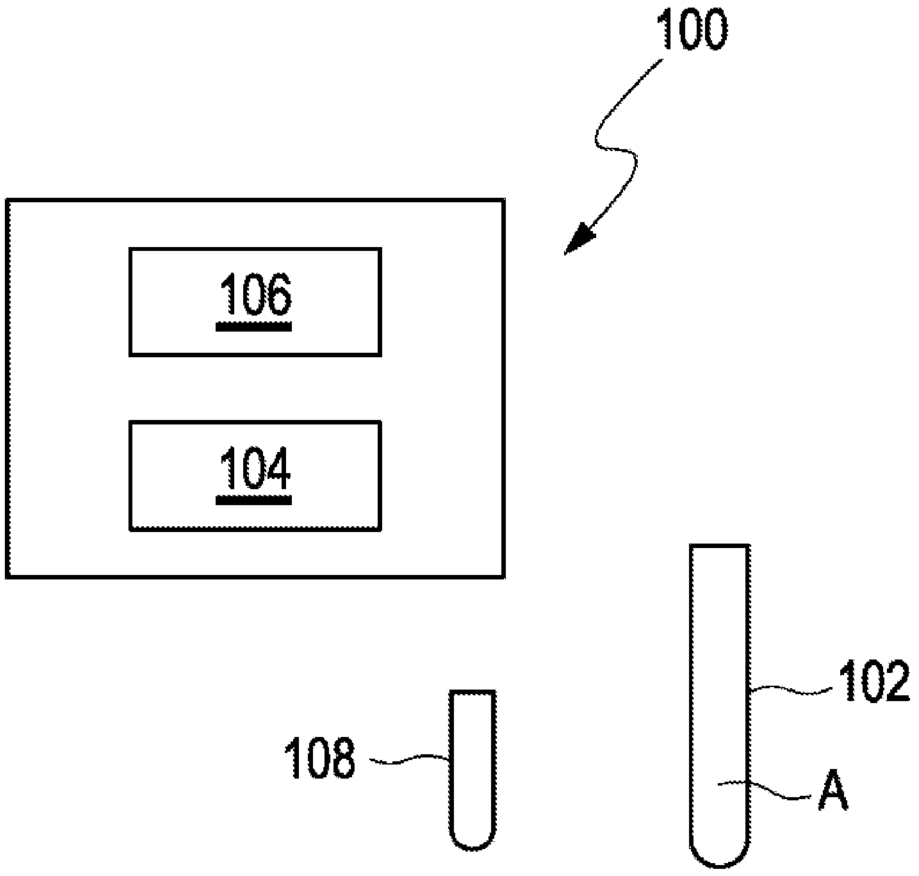
FIG. 1 shows an apparatus for determining a concentration of a target analyte in a sample of bodily fluid.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

The term "calibration" as used herein refers to a process of determining the relationship between an instrument response and an analyte concentration to ensure valid quantification of samples.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "particularly", "more particularly", "specifically", "more specifically" or similar terms are used in conjunction with features of particular or alternative embodiment(s), without restricting alternative possibilities. The disclosed method/system may, as the skilled person will recognize, be performed by using alternative features. Similarly, features introduced by "in an embodiment of the disclosed method/system" or similar expressions are intended to be additional and/or alternative features, without any restriction regarding alternative embodiments, without any restrictions regarding the scope of the disclosed method/system and without any restriction regarding the possibility of combining the features introduced in such way with other optional or non-optional features of the disclosed method/system.

According to the disclosed method, a method for determining a concentration of a target analyte in a sample of bodily fluid is disclosed. The method comprises the following steps:

- providing a sample of bodily fluid including the target analyte,
- providing an internal standard solution including a mixture of components comprising a plurality of isotopes of the target analyte, wherein a concentration of each isotope is unknown,
- adding the internal standard solution to the sample,
- analyzing the sample including the internal standard solution by means of a mass spectrometer,
- creating a sample function curve based on signal intensities, wherein the signal intensities define arbitrary units,
- transferring an analyte signal into a corresponding arbitrary analyte unit by means of the sample function curve, and
- transferring the arbitrary analyte unit into the concentration of a target analyte by means of a standardization function representing a curve of concentrations depending on the arbitrary units.

The term "target analyte" as used herein refers to any analyte of interest whose concentration is to be determined.

The term "internal standard solution" as used herein refers to a mixture of components having a different molecular weight than the target analyte. The concentration of the isotopes of the internal standard solution is unknown but tuned to give a signal intensity of the components between minimum signal and a maximum signal. An internal standard solution is essential for valid LC-MS quantification in complex matrices such as bodily fluid. This is a substance ideally identical to the target analyte and differs only in the molecular mass. With conventional mass spectrometry, the internal standard is typically used to produce a normalized instrument response based on the ratio of the analyte signal to an internal standard signal, i.e. the so called peak area ratio. With the disclosed method, the internal standard solution is used as an internal calibrator to enable internal calibration in each and every sample. This requires the assumption that a relative response factor is constant or that a relative response factor is corrected for by referencing external standards.

The term “calibration” as used herein refers to a process of determining the relationship between an instrument response and an analyte concentration to ensure valid quantification of samples.

The term “components” as used herein refers to a mixture of elements whose elements could be a mixture of natural isotope distribution from one chemical substance and/or a mixture of two or more chemical substances with individual isotope distribution.

The term “arbitrary unit” as used herein refers to any unit suitable to express a relation of the measured signal intensities to one another.

The term “standardization function” as used herein refers to a function that generates a lot specific function for each lot of the internal standard solution, and that describes the dependence of the concentration on the arbitrary units. The concentration is the analyte concentration in the sample in SI units such as mmol/l or mg/l.

With the disclosed method, the need for preparing exact concentrations of the components of the internal standard solution is avoided which saves costs and time. Rather, the key for transferring the arbitrary units resulting from the signal intensities into the concentration of the target analyte is provided by the standardization function which is externally provided beforehand and which is specific for each type of target analyte.

The standardization function may be created by means of analyzing patient samples, wherein each of the patient samples comprises a known concentration of the target analyte. Thus, it is ensured that the standardization function is created from the same biological matrix as the target sample. Therefore, any variation of the isotope distribution within the target sample and the sample basis for the creation of the standardization function is prevented.

The patient samples may be mixed with the internal standard solution. Thus, the patient samples comprise the same isotope distribution as the target sample.

The sample of bodily fluid may be provided with a predetermined volume. The internal standard solution may be added to the sample of bodily fluid with a predetermined volume. Thus, even though the concentration of the isotopes is unknown, an exact ratio of the internal standard solution and the sample is provided. Thereby, an exact calculation from the arbitrary units into the respective concentrations of the target analyte is facilitated.

The components may be ranked according to the signal intensities. Thus, even though the concentrations of the respective components are unknown, these are sorted according to their quantities relative to one another.

For example, the components are ranked from high intensity to low intensity. Needless to say, the components may alternatively be ranked from low intensity to high intensity.

The sample function curve may be created based on plotting the signal intensities depending on the arbitrary units. Thus, a correlation between the signal intensities and the arbitrary units is provided which allows to take further values representing arbitrary concentrations expressed by the arbitrary units from the sample function curve.

For example, the sample function curve is created by means of calculation from the plotted signal intensities.

The standardization function may be a polynomial function, an exponential function or partial linear function such as a piecewise linear function. These functions are well known and may thus be easily integrated into the disclosed method.

The patient samples may be measured according to a reference method. Thus, it is ensured that the standardization function is based on a standardized method which increases the reproducibility.

The standardization function may depend on the type of target analyte. Thus, the standardization function is adapted to the respective target analyte which ensures a reliable internal calibration depending on the respective target analyte.

The isotopes may be stable isotopes. Thus, stable measurement results are provided.

The sample of bodily fluid and the added internal standard solution may be analyzed in a single measurement by means of the mass spectrometer. Thus, the internal calibration process does not delay any analysis but is carried out at the same time as the analysis.

Further, an apparatus for determining a concentration of a target analyte in a sample of bodily fluid is disclosed. The apparatus comprises a mass spectrometer and a control unit configured to carry out the disclosed method.

The disclosed method further discloses and proposes a computer program including computer-executable instructions for performing the method according to the disclosed method in one or more of the embodiments enclosed herein when the program is executed on a computer or computer network. Specifically, the computer program may be stored on a computer-readable data carrier. Thus, specifically, one, more than one or even all of the method steps as indicated above may be performed by using a computer or a computer network, preferably by using a computer program.

The disclosed method further discloses and proposes a computer program product having program code means, in order to perform the method according to the disclosed method/system in one or more of the embodiments enclosed herein when the program is executed on a computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute the method according to one or more of the embodiments disclosed herein.

The invention further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing the method according to one or more of the embodiments disclosed herein.

Preferably, referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the disclosed method further discloses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Summarizing the findings of the disclosed method and apparatus, the following embodiments are disclosed:

Embodiment 1

Method for determining a concentration of a target analyte in a sample of bodily fluid, comprising:

providing a sample of bodily fluid including the target analyte, providing an internal standard solution including a mixture of components comprising a plurality of isotopes of the target analyte, wherein a concentration of each isotope is unknown, adding the internal standard solution to the sample, analyzing the sample including the internal standard solution by means of a mass spectrometer, creating a sample function curve based on signal intensities, wherein the signal intensities define arbitrary units, transferring an analyte signal into a corresponding arbitrary analyte unit by means of the sample function curve, and transferring the arbitrary analyte unit into the concentration of a target analyte by means of a standardization function representing a curve of concentrations depending on the arbitrary units.

Embodiment 2

Method according to embodiment 1, wherein the standardization function is created by means of analyzing patient samples, wherein each of the patient samples comprises a known concentration of the target analyte.

Embodiment 3

Method according to embodiment 2, wherein the patient samples are mixed with the internal standard solution.

Embodiment 4

Method according to any one of embodiments 1 to 3, wherein the sample of bodily fluid is provided with a predetermined volume, wherein the internal standard solution is added to the sample of bodily fluid with a predetermined volume.

Embodiment 5

Method according to any one of embodiments 1 to 4, wherein the components are ranked according to the signal intensities.

Embodiment 6

Method according to embodiment 5, wherein the components are ranked from high intensity to low intensity.

Embodiment 7

Method according to any one of embodiments 1 to 6, wherein the sample function curve is created based on plotting the signal intensities depending on the arbitrary units.

Embodiment 8

Method according to embodiment 7, wherein the sample function curve is created by means of calculation from the plotted signal intensities.

Embodiment 9

Method according to any one of embodiments 1 to 8, wherein the standardization function is a polynomial function, an exponential function or a partial linear function.

Embodiment 10

Method according to any one of embodiments 1 to 9, wherein the patient samples are measured according to a reference method.

Embodiment 11

Method according to any one of embodiments 1 to 10, wherein the standardization function depends on the type of target analyte.

Embodiment 12

Method according to any one of embodiments 1 to 11, wherein the isotopes are stable isotopes.

Embodiment 13

Method according to any one of embodiments 1 to 12, wherein the sample of bodily fluid and the added internal standard solution are analyzed in a single measurement by means of the mass spectrometer.

Embodiment 14

Apparatus for determining a concentration of a target analyte in a sample of bodily fluid, comprising mass spectrometer and a control unit configured to carry out the method according to any one of embodiments 1 to 13.

DETAILED DESCRIPTION OF THE EMBODIMENTS

FIG. 1 schematically shows an apparatus 100 for determining a concentration Ca of a target analyte A in a sample 102 of bodily fluid. The target analyte A may be testosterone. The bodily fluid may be blood. The apparatus 100 comprises a mass spectrometer 104 and a control unit 106. The control unit 106 is configured to carry out a method for determining the concentration Ca of the target analyte A in the sample 102 of bodily fluid. For this purpose, the control unit 104 cooperates with the mass spectrometer 102. The method is carried out as will be explained in further detail below.

Basically, the sample 102 of bodily fluid is provided. For example, blood from a patient is provided. Further, an internal standard solution 108 is provided. The internal standard solution 108 includes a mixture of components N1 to Nn comprising a plurality of isotopes of the target analyte. The isotopes differ in their molecular weight. Particularly, the isotopes are stable isotopes. A concentration of each isotope is unknown. The internal standard solution 108 is added to the sample 102. The sample 102 of bodily fluid is provided with a predetermined volume such as 25 ml and the internal standard solution 108 is added to the sample 102 of bodily fluid with a predetermined volume such as 5 ml. Subsequently, the sample 102 including the internal standard solution 108 is analyzed by means of the mass spectrometer 104. Particularly, the sample 102 of bodily fluid and the added internal standard solution 108 are analyzed in a single measurement by means of the mass spectrometer 104. Then, a sample function curve 110 based on signal intensities is created as will be explained in further detail hereinafter.

Figure 2:
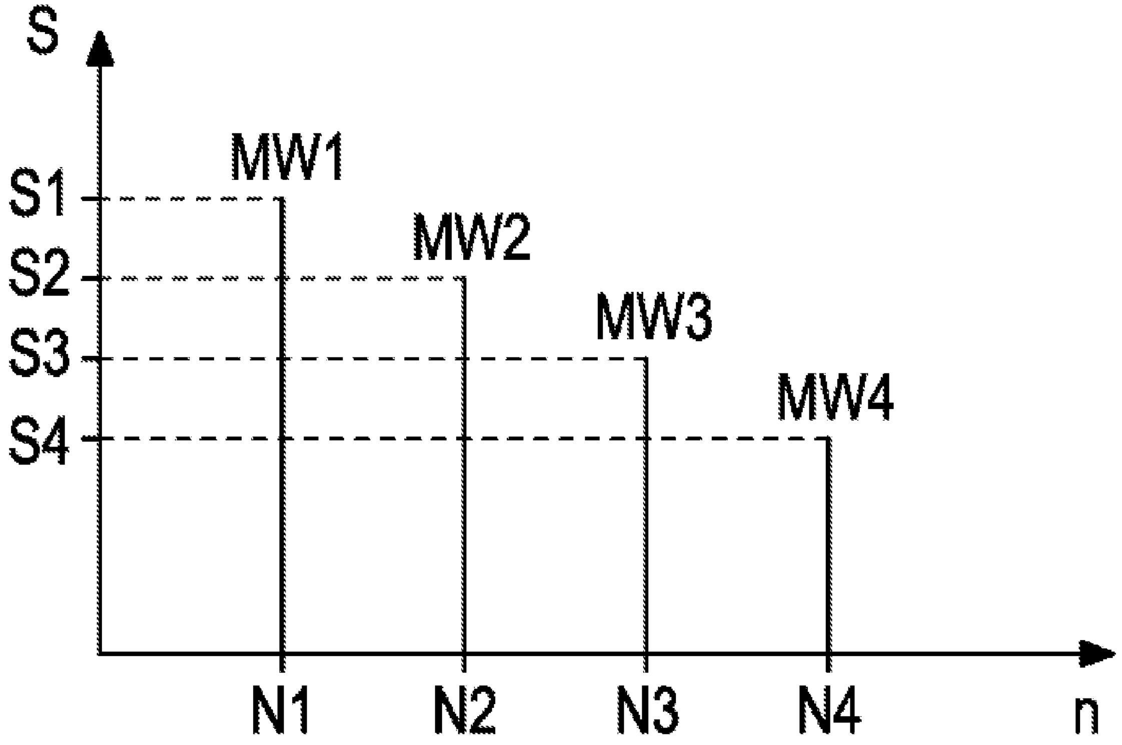
FIG. 2 shows a graph of signal intensities depending on the molecular weight.

FIG. 2 shows a graph of signal intensities depending on the molecular weight. The components are ranked according to the signal intensities. The components are ranked from high intensity to low intensity. For example, the internal standard solution 108 comprises 4 components N1, N2, N3, N4 in FIG. 2. Component N1 comprises a molecular weight MW1, component N2 comprises a molecular weight MW2, component N3 comprises a molecular weight MW3, and component N4 comprises a molecular weight MW4. The analyzed components N1, N2, N3, N4 result in signal intensities S1, S2, S3, S4.

Figure 3:
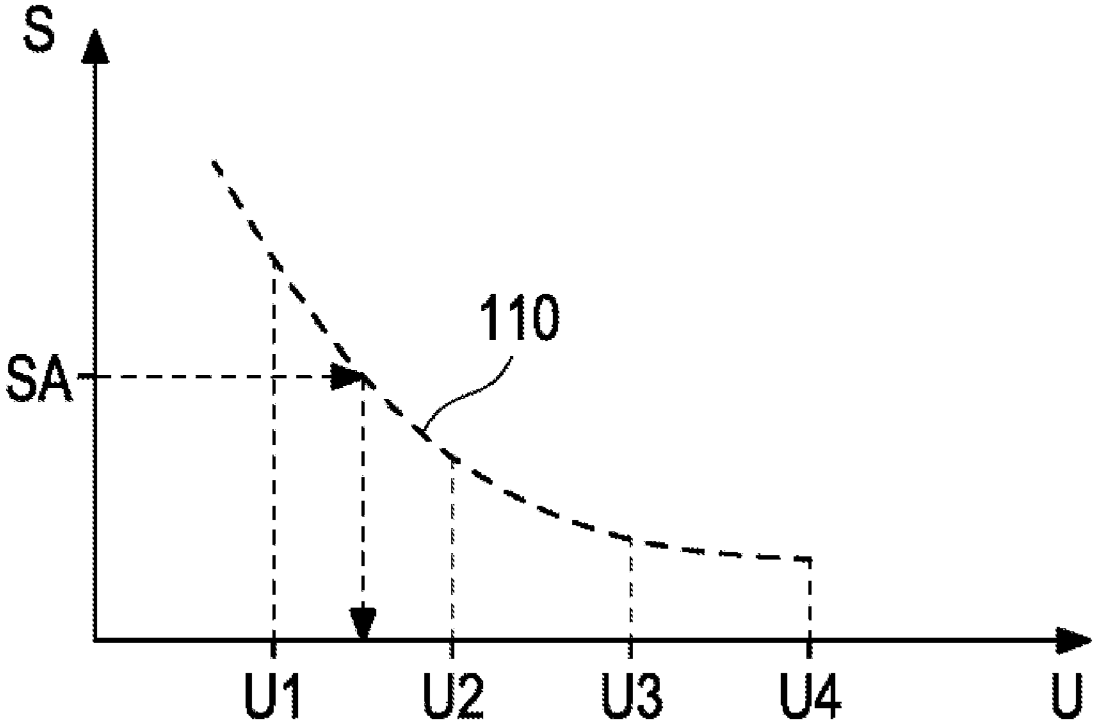
FIG. 3 shows a graph of signal intensities depending on arbitrary units.

FIG. 3 shows a graph of signal intensities depending on arbitrary units. The signal intensities S1, S2, S3, S4 define arbitrary units U1, U2, U3, U4. The sample function curve 110 is created based on plotting the signal intensities S1, S2, S3, S4 depending on the arbitrary units U1, U2, U3, U4. Particularly, the sample function curve 110 is created by means of calculation from the plotted signal intensities S1, S2, S3, S4. For example, the sample function curve 110 is created by means of interpolation of the arbitrary units U1, U2, U3, U4. The target analyte A also results in a signal SA. The analyte signal SA is transferred into a corresponding arbitrary analyte unit UA by means of the sample function curve 110. With other words, the signal SA is plotted on the y-axis. From this starting point an imaginary line parallel to the x-axis is drawn resulting in an interception point with the sample function curve 110. From this interception point an imaginary line parallel to the y-axis is drawn and the associated value on the x-axis results in the arbitrary analyte unit UA. In the example shown in FIG. 3, the arbitrary analyte unit UA corresponds to 1.6 arbitrary units U, i.e. 1.6 U.

Figure 4:
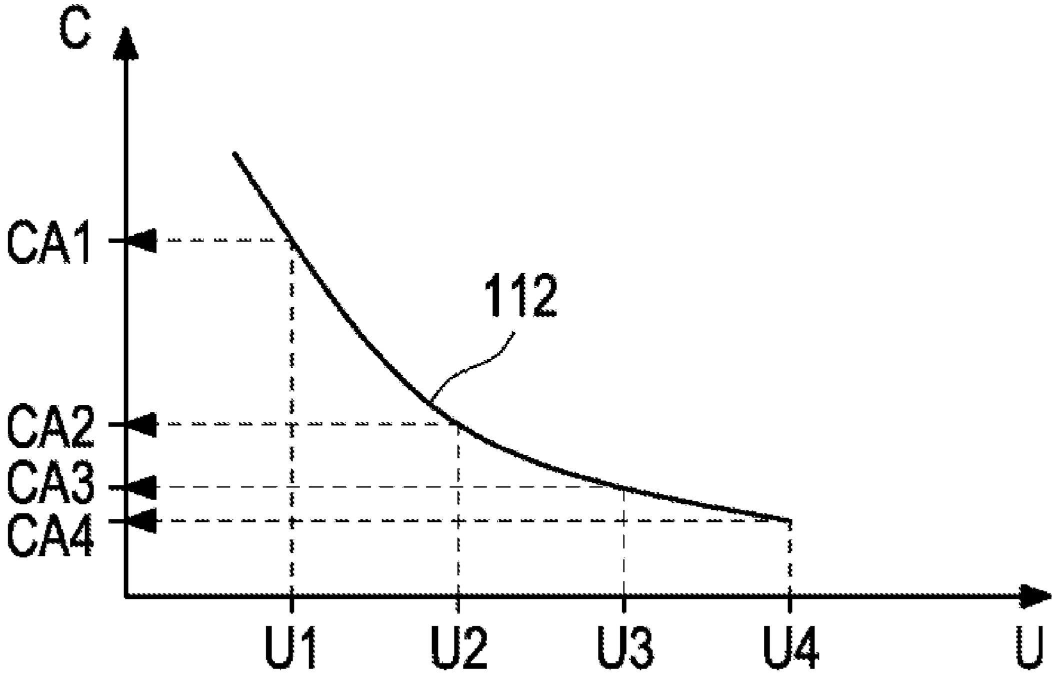
FIG. 4 shows a graph of concentrations depending on arbitrary units.

FIG. 4 shows a graph of concentrations depending on arbitrary units. This graph is a standardization function 112 representing a curve of concentrations CA1 to CAn depending on the arbitrary units U. The standardization function 112 is created by means of analyzing patient samples, wherein each of the patient samples comprises a known concentration CA1 to CAn of the target analyte A. It is to be noted that the patient samples are mixed with the internal standard solution 108. The standardization function 112 depends on the type of target analyte A. Therefore, the standardization function 112 is a polynomial function, an exponential function or a partial linear function. In order to generate the standardization function 112, the patient samples are measured according to a reference method. In the example shown in FIG. 4, the patient samples comprises a four known concentrations CA1, CA2, CA3, CA4 of the target analyte A, wherein each concentration CA1, CA2, CA3, CA4 a corresponding amount of arbitrary units U1, U2, U3, U4 is associated.

Figure 5:
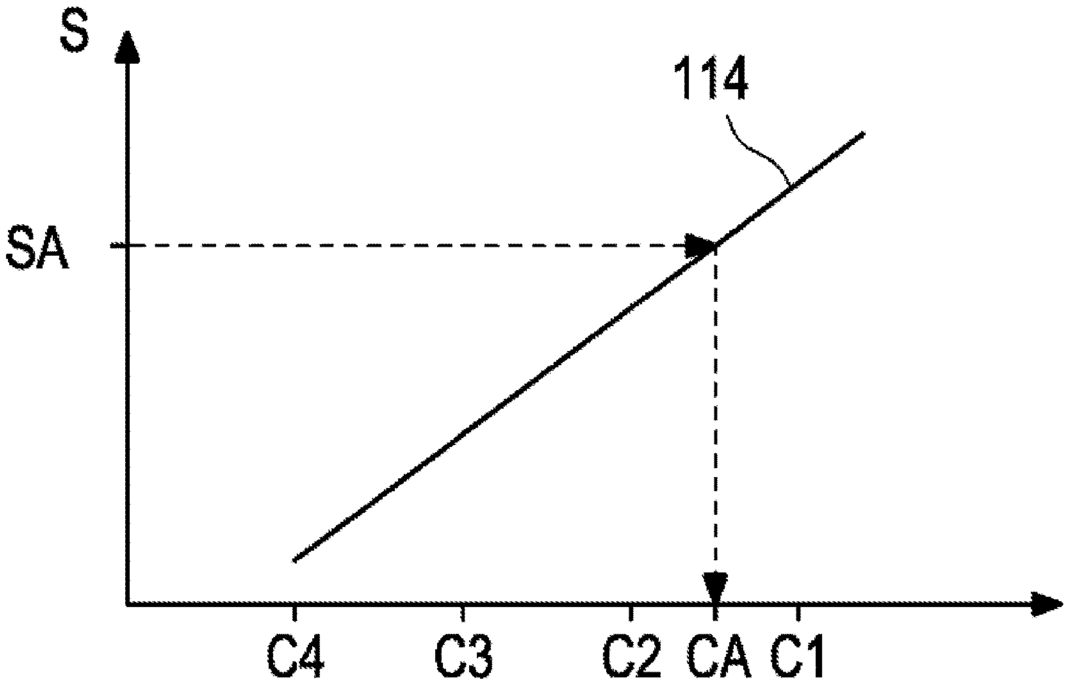
FIG. 5 a graph of signal intensities depending on concentrations.

FIG. 5 shows a graph of signal intensities depending on concentrations. By means of the standardization function 112, the signal intensity S of the analyzed sample 102 including the standard solution 108 may be transferred into concentrations C1 to Cn resulting in graph 114. Then, the arbitrary analyte unit UA is transferred into the concentration CA of the target analyte A by means of the standardization function 112. With other words, the signal SA is plotted on the y-axis. From this starting point an imaginary line parallel to the x-axis is drawn resulting in an interception point with the graph 114. From this interception point an imaginary line parallel to the y-axis is drawn and the associated value on the x-axis results in the concentration CA of the target analyte A.

The method of the present invention will be described in further detail based on the following examples. The examples were prepared by means of liquid chromatography coupled to mass spectrometry.

As a device for the liquid chromatography, an Agilent 1290 Infinity High Performance Liquid Chromatography (high performance liquid chromatography—HPLC) system was utilized to separate analytes from serum components before detection by means of mass spectrometry. The mobile Phase A was 2 mM ammonium acetate with 0.1% formic acid in water and the mobile phase B was 2 mM ammonium acetate with 0.1% formic acid in 95% acetonitrile and 5% water. For the column, a Phenomenex Kinetex 2.6u F5 100A, 150×2.1 mm (00F-4723-AN) was used. The following linear, step-wise gradient program was applied: 97% A/3% B to 95% A/5% B in 1.5 minutes, to 50% A/50% B in 0.3 minutes, to 0% A/100% B in 3.0 minutes, isocratic for 1.5 minutes, return to 97% A/3% B in 0.1 minutes and equilibrated for 1.1 minutes. The total run time was 7.4 minutes. The column oven was tempered at 40° C. and the samples were cooled at 8° C. in the autosampler. The injection volume was 50 μl and the needle was washed with 80% methanol and 20% water for 5 seconds in a flush port.

The mass spectrometer was an AB Sciex QTrap 6500 System (BL27421409) with Selexion FAIMS module. The ion source was a turbo spray ESI (ESI—electrospray ionization) with equal source parameters for positive and negative polarity: Temperature 300° C., curtain gas 30 psi, ion spray voltage ±4300 V, ion source gas 1 60 psi, ion source gas 2 30 psi and collision gas medium. The Selexion was operated under the following conditions: temperature low, no modifier, separation voltage 3500 V, and resolution enhancement open.

The analytes of the examples are given in table 1. Each analyte was tuned for optimal mass spectrometry voltage settings, i.e. declustering potential, collision energy, entrance potential, exit cell potential and compensation voltage. The following multiple reaction monitoring transitions were acquired and assigned to different internal standard functions. The isotope or multiple reaction monitoring transition corresponding to internal standard (IS) is used as the internal standard for the external calibration approach. All other isotopes of the internal standard were included for the internal calibration approach.

TABLE 1

| | Analyte | IS − 3 | IS − 2 | IS − 1 | IS | IS + 1 | IS + 2 | IS + 3 | IS + 4 |
|---|---|---|---|---|---|---|---|---|---|
| Testosterone | 289.2/109.2 | | | | 292.2/112.0 | 293.2/112.0 | 294.2/112.0 | | |
| Midazolam | 326.2/291.2 | | | | 332.2/297.2 | 333.2/297.2 | 334.2/297.2 | 335.2/297.2 | |
| Methamphetamine | 150.1/91.0 | | | 155.1/96.0 | 156.1/97.0 | 157.1/977.0 | | | |
| Nordiazepam | 271.2/208.1 | | | 276.2/213.1 | 277.2/214.1 | 278.2/215.1 | 279.2/214.1 | 280.2/215.1 | |
| Gabapentin | 172.1/67.0 | | | | 175.1/68.0 | 176.1/68.0 | 177.1/68.0 | | |
| Gentamicin 1 | 478.3/322.2 | | | | 481.3/324.2 | 482.3/324.2 | 483.3/324.2 | 484.3/324.2 | 485.3/324.2 |
| Chlordiazepoxide | 300.2/227.1 | | | 304.2/231.1 | 305.2/232.1 | 306.2/233.1 | 307.2/234.1 | 308.2/235.1 | |
| 5-Fluorouracil | 129.1/129.1 | | | | 132.1/132.1 | 133.1/133.1 | 134.1/134.1 | | |
| Valproic acid | 143.1/143.1 | | | | 146.1/146.1 | 147.1/147.1 | 148.1/148.1 | | |

Stock analyte solutions were prepared in a suitable solvent in higher concentration, either methanol, isopropanol or water. Spiked samples were then prepared by diluting the stock solutions in a vitamin D depleted human serum to gain the highest concentrated sample which is defined as 100%. From this working solution 7 calibration standards (Cal1 to Cal7) and 20 quality control samples (M01 to M20) were prepared ranging from 2%-100% of the working solution using the vitamin D depleted human serum as a diluent as given in table 2. Therein, the working solution is given in % and the sample concentrations are given in ng/ml.

TABLE 2

| Sample | % Working Solution | Testosterone | Midazolam | Chlordiazepoxide | Valproic Acid | Nordiazepam (ng/mL) | Gentamicin | 5-Fluoruracil | Gabapentin | Methamphetamine |
|---|---|---|---|---|---|---|---|---|---|---|
| M20 | 90% | 22.5 | 99 | 99 | 90000 | 135 | 22500 | 4500 | 900 | 108 |
| M19 | 80% | 20.0 | 88 | 88 | 80000 | 120 | 20000 | 4000 | 800 | 96 |
| M18 | 70% | 17.5 | 77 | 77 | 70000 | 105 | 17500 | 3500 | 700 | 84 |
| M17 | 60% | 15.0 | 66 | 66 | 60000 | 90 | 15000 | 3000 | 600 | 72 |
| M16 | 50% | 12.5 | 55 | 55 | 50000 | 75 | 12500 | 2500 | 500 | 60 |
| M15 | 40% | 10.0 | 44 | 44 | 40000 | 60 | 10000 | 2000 | 400 | 48 |
| M14 | 30% | 7.5 | 33 | 33 | 30000 | 45 | 7500 | 1500 | 300 | 36 |
| M13 | 20% | 5.0 | 22 | 22 | 20000 | 30 | 5000 | 1000 | 200 | 24 |
| M12 | 15% | 3.8 | 17 | 17 | 15000 | 23 | 3750 | 750 | 150 | 18 |
| M11 | 13% | 3.1 | 14 | 14 | 12500 | 19 | 3125 | 625 | 125 | 15 |
| M10 | 10% | 2.5 | 11 | 11 | 10000 | 15 | 2500 | 500 | 100 | 12 |
| M09 | 9% | 2.3 | 10 | 10 | 9000 | 14 | 2250 | 450 | 90 | 11 |

TABLE 2-continued

| Sample | % Working Solution | Testosterone | Midazolam | Chlordiazepoxide | Valproic Acid | Nordiazepam (ng/mL) | Gentamicin | 5-Fluoruracil | Gabapentin | Methamphetamine |
|---|---|---|---|---|---|---|---|---|---|---|
| M08 | 8% | 2.0 | 9 | 9 | 8000 | 12 | 2000 | 400 | 80 | 10 |
| M07 | 7% | 1.8 | 8 | 8 | 7000 | 11 | 1750 | 350 | 70 | 8 |
| M06 | 6% | 1.5 | 7 | 7 | 6000 | 9 | 1500 | 300 | 60 | 7 |
| M05 | 5% | 1.3 | 6 | 6 | 5000 | 8 | 1250 | 250 | 50 | 6 |
| M04 | 5% | 1.1 | 5 | 5 | 4500 | 7 | 1125 | 225 | 45 | 5 |
| M03 | 4% | 1.0 | 4 | 4 | 4000 | 6 | 1000 | 200 | 40 | 5 |
| M02 | 4% | 0.9 | 4 | 4 | 3500 | 5 | 875 | 175 | 35 | 4 |
| M01 | 3% | 0.8 | 3 | 3 | 3000 | 5 | 750 | 150 | 30 | 4 |
| Cal7 | 100% | 25.0 | 110 | 110 | 100000 | 150 | 25000 | 5000 | 1000 | 120 |
| Cal6 | 67% | 16.7 | 73 | 73 | 66667 | 100 | 16667 | 3333 | 667 | 80 |
| Cal5 | 44% | 11.1 | 49 | 49 | 44444 | 67 | 11111 | 2222 | 444 | 53 |
| Cal4 | 22% | 5.6 | 24 | 24 | 22222 | 33 | 5556 | 1111 | 222 | 27 |
| Cal3 | 11% | 2.8 | 12 | 12 | 11111 | 17 | 2778 | 556 | 111 | 13 |
| Cal2 | 6% | 1.4 | 6 | 6 | 5556 | 8 | 1389 | 278 | 56 | 7 |
| Cal1 | 3% | 0.7 | 3 | 3 | 2778 | 4 | 694 | 139 | 28 | 3 |

The internal standard mixture is prepared in 10 fold higher concentration than the 100% sample Cal7 shown in table 2. The samples were processed by adding 100 µl of each sample into a 1.5 ml Eppendorf cup followed by 10 µl of isotopically labelled internal standard. The sample was mixed for 10 minutes at 37° C. Then, 150 µl of acetonitrile was added to precipitate serum proteins. The sample was then vortexed for 10 minutes at 25° C. followed by a 1-hour incubation at 4° C.-8° C. Roughly 150 µl of supernatant was isolated and transferred to a HPLC vial after centrifuging the sample for 30 minutes at 14,000 rpm. The sample was further diluted by adding 150 µl water. Then, 5 µl of the sample was injected for LC-MS analysis. Each sample was analyzed 4 times to determine the intermediate precision.

The quality control samples M01 to M20 were quantified following the principle of external calibration. A full 7-point calibration was constructed and fitted with a linear curve using a 1/x weighting. This data evaluation is considered the state-of-the-art approach to which the internal multipoint calibration according to the present disclosure is to be compared to.

The quality control samples M01 to M20 were quantified following the principle of internal calibration based on isotope clusters of the internal standard as described above. The number of internal calibration points varied between 3 to 5 based on the analyte. The concentration of the isotopes was first standardized using a single analyte calibration standard. For this, the calibration standard Cal5 was chosen as it represents the middle of the target measuring range. The signal intensity of the individual isotopes was fitted against their concentration using a linear 1/x weighting function. The resulting isotope distribution of the thus prepared internal standards of the above analytes is shown in tables 3 to 10.

TABLE 3

| Testosterone $^{13}C_3$ | | | |
|---|---|---|---|
| Ion | m/z | Reference Material Abundance | Labelled Material Abundance |
| $[M+H]^+ - 2$ | 287.2 | 0.0% | 0.0% |
| $[M+H]^+ - 1$ | 288.2 | 0.0% | 0.0% |
| $[M+H]^+$ | 289.2 | 80.0% | 0.03% |
| $[M+H]^+ + 1$ | 290.2 | 17.7% | 0.0% |
| $[M+H]^+ + 2$ | 291.2 | 2.1% | 1.3% |
| $[M+H]^+ + 3$ | 292.2 | 0.1% | 80.1% |

TABLE 3-continued

| Testosterone $^{13}C_3$ | | | |
|---|---|---|---|
| Ion | m/z | Reference Material Abundance | Labelled Material Abundance |
| $[M+H]^+ + 4$ | 293.2 | 0.0% | 16.5% |
| $[M+H]^+ + 5$ | 294.2 | 0.0% | 1.8% |
| $[M+H]^+ + 6$ | 295.2 | 0.0% | 0.2% |
| $[M+H]^+ + 7$ | 296.2 | 0.0% | 0.1% |
| $[M+H]^+ + 8$ | 297.2 | 0.0% | 0.0% |
| $[M+H]^+ + 9$ | 298.2 | 0.0% | 0.0% |
| $[M+H]^+ + 10$ | 299.2 | 0.0% | 0.0% |
| $[M+H]^+ + 11$ | 300.2 | 0.0% | 0.0% |
| $[M+H]^+ + 12$ | 301.2 | 0.0% | 0.0% |
| $[M+H]^+ + 13$ | 302.2 | 0.0% | 0.0% |
| $[M+H]^+ + 14$ | 303.2 | 0.0% | 0.0% |
| $[M+H]^+ + 15$ | 304.2 | 0.0% | 0.0% |

TABLE 4

| Chlordiazepoxide $^2H_5$ | | | |
|---|---|---|---|
| Ion | m/z | Reference Material Abundance | Labelled Material Abundance |
| $[M+H]^+ - 2$ | 298.2 | 0.0% | 0.0% |
| $[M+H]^+ - 1$ | 299.2 | 2.2% | 0.0% |
| $[M+H]^+$ | 300.2 | 54.9% | 0.0% |
| $[M+H]^+ + 1$ | 301.2 | 13.6% | 0.0% |
| $[M+H]^+ + 2$ | 302.2 | 24.7% | 0.0% |
| $[M+H]^+ + 3$ | 303.2 | 4.1% | 0.0% |
| $[M+H]^+ + 4$ | 304.2 | 0.4% | 0.1% |
| $[M+H]^+ + 5$ | 305.2 | 0.0% | 3.8% |
| $[M+H]^+ + 6$ | 306.2 | 0.0% | 60.2% |
| $[M+H]^+ + 7$ | 307.2 | 0.0% | 9.6% |
| $[M+H]^+ + 8$ | 308.2 | 0.0% | 23.2% |
| $[M+H]^+ + 9$ | 309.2 | 0.1% | 2.9% |
| $[M+H]^+ + 10$ | 310.2 | 0.0% | 0.2% |
| $[M+H]^+ + 11$ | 311.2 | 0.0% | 0.0% |
| $[M+H]^+ + 12$ | 312.2 | 0.0% | 0.0% |
| $[M+H]^+ + 13$ | 313.2 | 0.0% | 0.0% |

TABLE 5

| Nordiazepam$^{13}C_6$ | | | |
|---|---|---|---|
| Ion | m/z | Reference Material Abundance | Labelled Material Abundance |
| $[M + H]^+ - 2$ | 269.2 | 0.0% | 0.0% |
| $[M + H]^+ - 1$ | 270.2 | 1.3% | 0.0% |
| $[M + H]^+$ | 271.2 | 62.3% | 0.03% |
| $[M + H]^+ + 1$ | 272.2 | 11.2% | 0.0% |
| $[M + H]^+ + 2$ | 273.2 | 21.5% | 0.0% |
| $[M + H]^+ + 3$ | 274.2 | 3.4% | 0.0% |
| $[M + H]^+ + 4$ | 275.2 | 0.3% | 0.1% |
| $[M + H]^+ + 5$ | 276.2 | 0.0% | 3.4% |
| $[M + H]^+ + 6$ | 277.2 | 0.0% | 63.6% |
| $[M + H]^+ + 7$ | 278.2 | 0.0% | 8.2% |
| $[M + H]^+ + 8$ | 279.2 | 0.0% | 22.2% |
| $[M + H]^+ + 9$ | 280.2 | 0.0% | 2.2% |
| $[M + H]^+ + 10$ | 281.2 | 0.0% | 0.2% |
| $[M + H]^+ + 11$ | 282.2 | 0.0% | 0.0% |
| $[M + H]^+ + 12$ | 283.2 | 0.0% | 0.0% |
| $[M + H]^+ + 13$ | 284.2 | 0.0% | 0.0% |

TABLE 6

| 5-Fluorouracil $^{13}C$, $^{15}N_2$ | | | |
|---|---|---|---|
| Ion | m/z | Reference Material Abundance | Labelled Material Abundance |
| $[M + H]^+ - 2$ | 127.1 | 0.0% | 0.1% |
| $[M + H]^+ - 1$ | 128.1 | 0.0% | 0.0% |
| $[M + H]^+$ | 129.1 | 95.2% | 0.11% |
| $[M + H]^+ + 1$ | 130.1 | 4.8% | 0.0% |
| $[M + H]^+ + 2$ | 131.1 | 0.0% | 1.6% |
| $[M + H]^+ + 3$ | 132.1 | 0.0% | 92.3% |
| $[M + H]^+ + 4$ | 133.1 | 0.0% | 3.6% |
| $[M + H]^+ + 5$ | 134.1 | 0.0% | 2.2% |
| $[M + H]^+ + 6$ | 135.1 | 0.0% | 0.1% |
| $[M + H]^+ + 7$ | 136.1 | 0.0% | 0.0% |
| $[M + H]^+ + 8$ | 137.1 | 0.0% | 0.0% |
| $[M + H]^+ + 9$ | 138.1 | 0.0% | 0.0% |
| $[M + H]^+ + 10$ | 139.1 | 0.0% | 0.0% |

TABLE 7

| Valproic Acid $^{13}C_4$ | | | |
|---|---|---|---|
| Ion | m/z | Reference Material Abundance | Labelled Material Abundance |
| $[M + H]^+ - 2$ | 141.1 | 0.0% | 0.0% |
| $[M + H]^+ - 1$ | 142.1 | 0.0% | 0.1% |
| $[M + H]^+$ | 143.1 | 90.6% | 0.2% |
| $[M + H]^+ + 1$ | 144.1 | 8.1% | 0.0% |
| $[M + H]^+ + 2$ | 145.1 | 1.2% | 1.3% |
| $[M + H]^+ + 3$ | 146.1 | 0.0% | 2.2% |
| $[M + H]^+ + 4$ | 147.1 | 0.0% | 90.3% |
| $[M + H]^+ + 5$ | 148.1 | 0.0% | 4.7% |
| $[M + H]^+ + 6$ | 149.1 | 0.0% | 0.4% |
| $[M + H]^+ + 7$ | 150.1 | 0.0% | 0.0% |
| $[M + H]^+ + 8$ | 151.1 | 0.0% | 0.4% |
| $[M + H]^+ + 9$ | 152.1 | 0.0% | 0.1% |
| $[M + H]^+ + 10$ | 153.1 | 0.0% | 0.1% |
| $[M + H]^+ + 11$ | 154.1 | 0.0% | 0.0% |

TABLE 8

| Gabapentin $^{13}C_3$ | | | |
|---|---|---|---|
| Ion | m/z | Reference Material Abundance | Labelled Material Abundance |
| $[M + H]^+ - 2$ | 170.1 | 0.1% | 0.1% |
| $[M + H]^+ - 1$ | 171.1 | 0.0% | 0.0% |
| $[M + H]^+$ | 172.1 | 76.9% | 0.1% |
| $[M + H]^+ + 1$ | 173.1 | 20.8% | 0.0% |
| $[M + H]^+ + 2$ | 174.1 | 1.8% | 2.5% |
| $[M + H]^+ + 3$ | 175.1 | 0.1% | 82.8% |
| $[M + H]^+ + 4$ | 176.1 | 0.1% | 13.3% |
| $[M + H]^+ + 5$ | 177.1 | 0.0% | 1.1% |
| $[M + H]^+ + 6$ | 178.1 | 0.0% | 0.1% |
| $[M + H]^+ + 7$ | 179.1 | 0.0% | 0.0% |
| $[M + H]^+ + 8$ | 180.1 | 0.1% | 0.0% |
| $[M + H]^+ + 9$ | 181.1 | 0.0% | 0.0% |
| $[M + H]^+ + 10$ | 182.1 | 0.0% | 0.0% |

TABLE 9

| Methamphetamine $^{13}C_6$ | | | |
|---|---|---|---|
| Ion | m/z | Reference Material Abundance | Labelled Material Abundance |
| $[M + H]^+ - 2$ | 148.1 | 0.0% | 0.0% |
| $[M + H]^+ - 1$ | 149.1 | 0.0% | 0.0% |
| $[M + H]^+$ | 150.1 | 90.2% | 0.1% |
| $[M + H]^+ + 1$ | 151.1 | 9.3% | 0.0% |
| $[M + H]^+ + 2$ | 152.1 | 0.4% | 0.0% |
| $[M + H]^+ + 3$ | 153.1 | 0.0% | 0.0% |
| $[M + H]^+ + 4$ | 154.1 | 0.0% | 0.2% |
| $[M + H]^+ + 5$ | 155.1 | 0.0% | 5.3% |
| $[M + H]^+ + 6$ | 156.1 | 0.0% | 90.1% |
| $[M + H]^+ + 7$ | 157.1 | 0.0% | 4.2% |
| $[M + H]^+ + 8$ | 158.1 | 0.0% | 0.0% |
| $[M + H]^+ + 9$ | 159.1 | 0.0% | 0.0% |
| $[M + H]^+ + 10$ | 160.1 | 0.0% | 0.0% |
| $[M + H]^+ + 11$ | 161.1 | 0.0% | 0.0% |
| $[M + H]^+ + 12$ | 162.1 | 0.0% | 0.0% |
| $[M + H]^+ + 13$ | 163.1 | 0.0% | 0.0% |

TABLE 10

| Gentamicin C1-deuterated | | | |
|---|---|---|---|
| Ion | m/z | Reference Material Abundance | Labelled Material Abundance |
| $[M + H]^+$ | 478.3 | 71.6% | 0.0% |
| $[M + H]^+ + 1$ | 479.3 | 23.7% | 4.7% |
| $[M + H]^+ + 2$ | 480.3 | 3.7% | 28.7% |
| $[M + H]^+ + 3$ | 481.3 | 0.6% | 29.0% |
| $[M + H]^+ + 4$ | 482.3 | 0.1% | 17.3% |
| $[M + H]^+ + 5$ | 483.3 | 0.1% | 11.5% |
| $[M + H]^+ + 6$ | 484.3 | 0.1% | 5.9% |
| $[M + H]^+ + 7$ | 485.3 | 0.0% | 2.1% |
| $[M + H]^+ + 8$ | 486.3 | 0.1% | 0.6% |
| $[M + H]^+ + 9$ | 487.3 | 0.0% | 0.2% |
| $[M + H]^+ + 10$ | 488.3 | 0.0% | 0.1% |

In tables 3 to 10, the first column from the left gives the respective isotopes indicated as ions. The second column from the left gives the molecular weight of the isotopes. The third column from the left gives the relative contents of the isotopes of a reference material indicated as reference material abundance. The fourth column from the left gives the relative contents of the isotopes of the labelled material prepared as described above and indicated as labelled material abundance.

The reference materials and internal standards, respectively, as indicated in tables 3 to 10, the tradename thereof and the respective source of supply are given in table 11.

TABLE 11

| Reference Material | Trade Name | Source of Supply |
|---|---|---|
| Testosterone 13C3 | IsoSciences 6066 | IsoSciences, 1017 W 9th Ave King of Prussia, Pennsylvania 19406, USA |
| Chlordiazepoxide d5 | Cerilliant C-912 | Cerilliant Corporation, 811 Paloma Drive, Suite A, Round Rock, Texas 78665, USA |
| Nordiazepam 13C6 | AlsaChim C2096 | ALSACHIM, Bioparc, Boulevard Sébastien Brandt, 67400 Illkirch Graffenstaden, France |
| 5-Fluoruracil C13, 2 × N15 | Sigma 723258 | Sigma-Aldrich Corporation, 3050 Spruce St, St. Louis, Missouri 63103, USA |
| Valproic Acid 13C4 sodium salt | Sigma 630101 | Sigma-Aldrich Corporation, 3050 Spruce St, St. Louis, Missouri 63103, USA |
| Gabapentin 13C3 | Cerilliant G-018-1ML | Cerilliant Corporation, 811 Paloma Drive, Suite A, Round Rock, Texas 78665, USA |
| Methamphetamine 13C6 | Chiron AS 9677.10-K-ME | Chiron AS, Stiklestadveien 1, N-7041 Trondheim, Norway |
| Gentamicin deuterated pentaacetate salt | TRC G360602 | Toronto Research Chemicals, 2 Brisbane Rd., Toronto, Ontario, Canada |
| Testosterone | Sigma 86500-5G | Sigma-Aldrich Corporation, 3050 Spruce St, St. Louis, Missouri 63103, USA |
| Chlordiazepoxid-Hydrochlorid | Sigma C-2517 | Sigma-Aldrich Corporation, 3050 Spruce St, St. Louis, Missouri 63103, USA |
| Nordiazepam | Sigma D-7282 | Sigma-Aldrich Corporation, 3050 Spruce St, St. Louis, Missouri 63103, USA |
| 5-Fluorouracil | Sigma 03738 | Sigma-Aldrich Corporation, 3050 Spruce St, St. Louis, Missouri 63103, USA |
| Valproic Acid | Sigma V0033000 | Sigma-Aldrich Corporation, 3050 Spruce St, St. Louis, Missouri 63103, USA |
| Gabapentin | Sigma G154 | Sigma-Aldrich Corporation, 3050 Spruce St, St. Louis, Missouri 63103, USA |
| Methamphetamin-Hydrochlorid | Sigma M-8750 | Sigma-Aldrich Corporation, 3050 Spruce St, St. Louis, Missouri 63103, USA |
| Gentamicin Sulphate | United States Biological; Gentamycin Sulfate USP, G2030 | United States Biological, 4 Technology Way Salem, Massachusetts 01970, USA |

As can be taken from tables 3 to 10, a series of isotope labelled analytes can be feasibly realized and utilized to perform an internal calibration based on LC-MS analysis. It is apparent that isotopically labelled internal standards are actually a distribution of many different isotopic structures and isotope clusters, respectively, due to either the natural isotopic distribution or by synthetic alterations. This distribution as shown in tables 3 to 10 is apparent in every single small molecule and remains also present when synthetically labelling small molecules. It is also apparent that the individual isotopes all have a unique abundance or concentration.

The measuring results of samples M01 to M20 of the analytes based on external calibration and based on the disclosed method including an internal multipoint calibration are given in tables 12 to 20.

TABLE 12

| | | External Calibration 7 Point | | Internal Multipoint Calibration | | |
|---|---|---|---|---|---|---|
| Analyte | Sample | Measured Concentration (ng/mL) | Precision (CV) | Measured Concentration (ng/mL) | Precision (CV) | Accuracy (relative to Ext) |
| 5-Fluorouracil | S01 | 240 | 4% | 267 | 4% | 11% |
| | S02 | 254 | 3% | 271 | 4% | 7% |
| | S03 | 295 | 5% | 314 | 6% | 6% |
| | S04 | 326 | 12% | 342 | 9% | 5% |
| | S05 | 344 | 7% | 359 | 6% | 5% |
| | S06 | 382 | 2% | 395 | 3% | 3% |
| | S07 | 437 | 6% | 449 | 4% | 3% |
| | S08 | 494 | 4% | 501 | 4% | 1% |
| | S09 | 543 | 5% | 545 | 5% | 0% |
| | S10 | 571 | 2% | 570 | 2% | 0% |
| | S11 | 710 | 4% | 698 | 3% | −2% |
| | S12 | 830 | 2% | 810 | 1% | −2% |
| | S13 | 1039 | 2% | 1006 | 2% | −3% |
| | S14 | 1547 | 2% | 1478 | 2% | −4% |
| | S15 | 2028 | 2% | 1923 | 2% | −5% |
| | S16 | 2465 | 2% | 2336 | 2% | −5% |
| | S17 | 3080 | 1% | 2904 | 1% | −6% |
| | S18 | 3425 | 2% | 3225 | 2% | −6% |

TABLE 12-continued

| Analyte | Sample | External Calibration 7 Point Measured Concentration (ng/mL) | External Calibration 7 Point Precision (CV) | Internal Multipoint Calibration Measured Concentration (ng/mL) | Internal Multipoint Calibration Precision (CV) | Internal Multipoint Calibration Accuracy (relative to Ext) |
|---|---|---|---|---|---|---|
| | S19 | 4069 | 1% | 3825 | 1% | −6% |
| | S20 | 4578 | 2% | 4293 | 2% | −6% |

TABLE 13

| Analyte | Sample | External Calibration 7 Point Measured Concentration (ng/mL) | External Calibration 7 Point Precision (CV) | Internal Multipoint Calibration Measured Concentration (ng/mL) | Internal Multipoint Calibration Precision (CV) | Internal Multipoint Calibration Accuracy (relative to Ext) |
|---|---|---|---|---|---|---|
| Chlordiazepoxide | S01 | 3 | 10% | 3 | 8% | 11% |
| | S02 | 4 | 6% | 4 | 5% | 8% |
| | S03 | 4 | 9% | 4 | 8% | 7% |
| | S04 | 5 | 9% | 5 | 8% | 5% |
| | S05 | 5 | 10% | 5 | 10% | 3% |
| | S06 | 6 | 9% | 7 | 7% | 3% |
| | S07 | 8 | 10% | 8 | 9% | 1% |
| | S08 | 8 | 5% | 8 | 6% | 2% |
| | S09 | 10 | 10% | 10 | 9% | 0% |
| | S10 | 11 | 2% | 11 | 2% | 0% |
| | S11 | 14 | 5% | 13 | 4% | −1% |
| | S12 | 17 | 4% | 16 | 3% | −2% |
| | S13 | 21 | 4% | 21 | 4% | −2% |
| | S14 | 30 | 5% | 30 | 6% | −2% |
| | S15 | 41 | 6% | 40 | 5% | −3% |
| | S16 | 51 | 2% | 49 | 3% | −4% |
| | S17 | 65 | 1% | 63 | 2% | −4% |
| | S18 | 75 | 1% | 72 | 2% | −3% |
| | S19 | 85 | 4% | 82 | 5% | −4% |
| | S20 | 93 | 5% | 90 | 5% | −3% |

TABLE 14

| Analyte | Sample | External Calibration 7 Point Measured Concentration (ng/mL) | External Calibration 7 Point Precision (CV) | Internal Multipoint Calibration Measured Concentration (ng/mL) | Internal Multipoint Calibration Precision (CV) | Internal Multipoint Calibration Accuracy (relative to Ext) |
|---|---|---|---|---|---|---|
| Gabapentin | S01 | 32 | 7% | 30 | 9% | −4% |
| | S02 | 36 | 4% | 35 | 5% | −5% |
| | S03 | 42 | 3% | 41 | 3% | −4% |
| | S04 | 49 | 3% | 47 | 3% | −3% |
| | S05 | 54 | 1% | 52 | 1% | −3% |
| | S06 | 64 | 3% | 62 | 3% | −3% |
| | S07 | 74 | 2% | 72 | 2% | −3% |
| | S08 | 82 | 4% | 79 | 4% | −3% |
| | S09 | 96 | 2% | 93 | 1% | −3% |
| | S10 | 104 | 2% | 101 | 2% | −3% |
| | S11 | 128 | 3% | 125 | 3% | −3% |
| | S12 | 150 | 5% | 146 | 5% | −2% |
| | S13 | 201 | 2% | 197 | 2% | −2% |
| | S14 | 303 | 2% | 297 | 3% | −2% |
| | S15 | 405 | 1% | 397 | 1% | −2% |
| | S16 | 490 | 2% | 479 | 1% | −2% |
| | S17 | 628 | 3% | 614 | 3% | −2% |
| | S18 | 710 | 2% | 696 | 2% | −2% |
| | S19 | 835 | 2% | 818 | 2% | −2% |
| | S20 | 917 | 3% | 899 | 3% | −2% |

TABLE 15

| Analyte | Sample | External Calibration 7 Point Measured Concentration (ng/mL) | External Calibration 7 Point Precision (CV) | Internal Multipoint Calibration Measured Concentration (ng/mL) | Internal Multipoint Calibration Precision (CV) | Internal Multipoint Calibration Accuracy (relative to Ext) |
|---|---|---|---|---|---|---|
| Gentamicin | S01 | 577 | 8% | 567 | 7% | −2% |
| | S02 | 635 | 4% | 619 | 4% | −3% |
| | S03 | 719 | 6% | 706 | 6% | −2% |
| | S04 | 854 | 3% | 828 | 2% | −3% |
| | S05 | 930 | 4% | 898 | 4% | −3% |
| | S06 | 1063 | 5% | 1021 | 4% | −4% |
| | S07 | 1271 | 3% | 1211 | 3% | −5% |
| | S08 | 1487 | 3% | 1404 | 2% | −6% |
| | S09 | 1623 | 2% | 1536 | 2% | −5% |
| | S10 | 1809 | 4% | 1703 | 5% | −6% |
| | S11 | 2241 | 4% | 2116 | 4% | −6% |
| | S12 | 2743 | 2% | 2555 | 2% | −7% |
| | S13 | 3496 | 4% | 3277 | 5% | −6% |
| | S14 | 5200 | 5% | 4844 | 5% | −7% |
| | S15 | 7122 | 6% | 6600 | 5% | −7% |
| | S16 | 8723 | 4% | 8068 | 4% | −8% |
| | S17 | 10974 | 4% | 10171 | 4% | −7% |
| | S18 | 12545 | 3% | 11621 | 3% | −7% |
| | S19 | 14161 | 3% | 13080 | 3% | −8% |
| | S20 | 15736 | 5 | 14645 | 4% | −7% |

TABLE 16

| Analyte | Sample | External Calibration 7 Point Measured Concentration (ng/mL) | External Calibration 7 Point Precision (CV) | Internal Multipoint Calibration Measured Concentration (ng/mL) | Internal Multipoint Calibration Precision (CV) | Internal Multipoint Calibration Accuracy (relative to Ext) |
|---|---|---|---|---|---|---|
| Mthamphetamine | S01 | 4 | 4% | 3 | 2% | −15% |
| | S02 | 4 | 6% | 4 | 11% | −9% |
| | S03 | 5 | 4% | 4 | 6% | −10% |
| | S04 | 6 | 2% | 5 | 6% | −10% |
| | S05 | 6 | 4% | 6 | 5% | −8% |
| | S06 | 8 | 4% | 7 | 3% | −7% |
| | S07 | 9 | 3% | 8 | 3% | −7% |
| | S08 | 10 | 5% | 9 | 5% | −5% |
| | S09 | 11 | 3% | 10 | 4% | −6% |
| | S10 | 12 | 3% | 12 | 4% | −5% |
| | S11 | 16 | 4% | 15 | 4% | −5% |
| | S12 | 18 | 4% | 17 | 4% | −4% |
| | S13 | 24 | 3% | 23 | 3% | −3% |
| | S14 | 35 | 1% | 34 | 2% | −3% |
| | S15 | 48 | 3% | 47 | 3% | −3% |
| | S16 | 58 | 2% | 56 | 2% | −3% |
| | S17 | 73 | 3% | 71 | 3% | −3% |
| | S18 | 84 | 2% | 81 | 2% | −3% |
| | S19 | 97 | 1% | 94 | 1% | −3% |
| | S20 | 108 | 2% | 105 | 2% | −3% |

TABLE 17

| Analyte | Sample | External Calibration 7 Point Measured Concentration (ng/mL) | External Calibration 7 Point Precision (CV) | Internal Multipoint Calibration Measured Concentration (ng/mL) | Internal Multipoint Calibration Precision (CV) | Internal Multipoint Calibration Accuracy (relative to Ext) |
|---|---|---|---|---|---|---|
| Midazolam | S01 | 4 | 8% | 3 | 7% | −15% |
| | S02 | 4 | 5% | 3 | 6% | −15% |
| | S03 | 5 | 5% | 4 | 3% | −12% |
| | S04 | 5 | 5% | 5 | 3% | −9% |

TABLE 17-continued

| | | External Calibration 7 Point | | Internal Multipoint Calibration | | |
|---|---|---|---|---|---|---|
| Analyte | Sample | Measured Concentration (ng/mL) | Precision (CV) | Measured Concentration (ng/mL) | Precision (CV) | Accuracy (relative to Ext) |
| | S05 | 6 | 2% | 5 | 3% | −10% |
| | S06 | 6 | 7% | 6 | 5% | −10% |
| | S07 | 8 | 2% | 7 | 2% | −9% |
| | S08 | 9 | 3% | 8 | 2% | −8% |
| | S09 | 10 | 1% | 9 | 1% | −7% |
| | S10 | 11 | 2% | 10 | 2% | −7% |
| | S11 | 13 | 3% | 12 | 3% | −6% |
| | S12 | 16 | 5% | 15 | 3% | −7% |
| | S13 | 21 | 6% | 20 | 5% | −6% |
| | S14 | 31 | 3% | 29 | 2% | −5% |
| | S15 | 42 | 5% | 40 | 5% | −5% |
| | S16 | 51 | 6% | 48 | 7% | −6% |
| | S17 | 61 | 6% | 59 | 7% | −4% |
| | S18 | 77 | 3% | 73 | 5% | −5% |
| | S19 | 82 | 5% | 78 | 7% | −5% |
| | S20 | 94 | 5% | 89 | 5% | −6% |

TABLE 18

| | | External Calibration 7 Point | | Internal Multipoint Calibration | | |
|---|---|---|---|---|---|---|
| Analyte | Sample | Measured Concentration (ng/mL) | Precision (CV) | Measured Concentration (ng/mL) | Precision (CV) | Accuracy (relative to Ext) |
| Nordizepam | S01 | 4 | 10% | 4 | 11% | 1% |
| | S02 | 6 | 8% | 5 | 7% | −3% |
| | S03 | 5 | 12% | 6 | 8% | 4% |
| | S04 | 7 | 5% | 7 | 4% | −1% |
| | S05 | 7 | 5% | 7 | 9% | −1% |
| | S06 | 8 | 7% | 9 | 9% | 2% |
| | S07 | 10 | 14% | 10 | 8% | −3% |
| | S08 | 11 | 6% | 11 | 4% | −2% |
| | S09 | 13 | 12% | 13 | 7% | −4% |
| | S10 | 14 | 8% | 14 | 8% | −2% |
| | S11 | 18 | 6% | 18 | 7% | 0% |
| | S12 | 21 | 8% | 21 | 8% | −3% |
| | S13 | 27 | 9% | 28 | 5% | 0% |
| | S14 | 43 | 2% | 40 | 4% | −5% |
| | S15 | 57 | 4% | 57 | 2% | −1% |
| | S16 | 66 | 12% | 67 | 10% | 2% |
| | S17 | 86 | 2% | 85 | 4% | −1% |
| | S18 | 103 | 7% | 99 | 1% | −4% |
| | S19 | 113 | 6% | 114 | 5% | 0% |
| | S20 | 140 | 6% | 130 | 4% | −7% |

TABLE 19

| | | External Calibration 7 Point | | Internal Multipoint Calibration | | |
|---|---|---|---|---|---|---|
| Analyte | Sample | Measured Concentration (ng/mL) | Precision (CV) | Measured Concentration (ng/mL) | Precision (CV) | Accuracy (relative to Ext) |
| Testosterne | S01 | 7 | 27% | 6 | 25% | −9% |
| | S02 | 6 | 16% | 6 | 16% | −10% |
| | S03 | 6 | 11% | 5 | 11% | −9% |
| | S04 | 7 | 5% | 7 | 4% | −11% |
| | S05 | 6 | 6% | 5 | 6% | −9% |
| | S06 | 6 | 10% | 6 | 11% | −9% |
| | S07 | 7 | 6% | 7 | 6% | −10% |
| | S08 | 7 | 13% | 6 | 11% | −9% |

TABLE 19-continued

| | | External Calibration 7 Point | | Internal Multipoint Calibration | | |
|---|---|---|---|---|---|---|
| Analyte | Sample | Measured Concentration (ng/mL) | Precision (CV) | Measured Concentration (ng/mL) | Precision (CV) | Accuracy (relative to Ext) |
| | S09 | 8 | 13% | 7 | 14% | −9% |
| | S10 | 7 | 14% | 7 | 12% | −7% |
| | S11 | 7 | 10% | 7 | 9% | −9% |
| | S12 | 9 | 8% | 8 | 7% | −10% |
| | S13 | 10 | 12% | 9 | 11% | −9% |
| | S14 | 10 | 8% | 9 | 9% | −8% |
| | S15 | 14 | 8% | 12 | 9% | −9% |
| | S16 | 15 | 5% | 14 | 3% | −10% |
| | S17 | 16 | 16% | 14 | 16% | −9% |
| | S18 | 19 | 10% | 17 | 8% | −10% |
| | S19 | 22 | 8% | 20 | 7% | −9% |
| | S20 | 24 | 15% | 22 | 14% | −9% |

TABLE 20

| | | External Calibration 7 Point | | Internal Multipoint Calibration | | |
|---|---|---|---|---|---|---|
| Analyte | Sample | Measured Concentration (ng/mL) | Precision (CV) | Measured Concentration (ng/mL) | Precision (CV) | Accuracy (relative to Ext) |
| Valproic Acid | S01 | 2595 | 8% | 3186 | 5% | 23% |
| | S02 | 3111 | 12% | 3793 | 16% | 22% |
| | S03 | 3817 | 17% | 4564 | 11% | 20% |
| | S04 | 4842 | 21% | 5321 | 24% | 10% |
| | S05 | 6291 | 11% | 6919 | 8% | 10% |
| | S06 | 6070 | 21% | 6946 | 22% | 14% |
| | S07 | 6779 | 8% | 7181 | 12% | 6% |
| | S08 | 8752 | 14% | 9585 | 13% | 10% |
| | S09 | 7965 | 11% | 8873 | 9% | 11% |
| | S10 | 9298 | 9% | 9843 | 8% | 6% |
| | S11 | 11553 | 9% | 12325 | 6% | 7% |
| | S12 | 14631 | 7% | 15424 | 5% | 5% |
| | S13 | 20119 | 6% | 20122 | 6% | 0% |
| | S14 | 28385 | 7% | 28821 | 7% | 2% |
| | S15 | 35710 | 6% | 35491 | 6% | −1% |
| | S16 | 45490 | 7% | 45118 | 6% | −1% |
| | S17 | 59103 | 3% | 57999 | 3% | −2% |
| | S18 | 64649 | 5% | 63752 | 5% | −1% |
| | S19 | 79495 | 5% | 77797 | 4% | −2% |
| | S20 | 84414 | 4% | 82802 | 4% | −2% |

In tables 12 to 20, the first column from the left gives the analyte. The second column from the left gives the sample. The third column from the left gives the measured concentration in ng/ml according to external calibration. The fourth column from the left gives the precision in percent coefficient of variation according to external calibration. The fifth column gives the measured concentration in ng/ml according to the disclosed method including internal multipoint calibration. The sixth column from the left gives the precision in percent coefficient of variation according to the disclosed method including internal multipoint calibration. The seventh column from the left gives the accuracy according to the disclosed method including internal multipoint calibration relative to the external calibration.

As can be taken from tables 12 to 20, the isotopes of the analytes can be used as internal calibrators to perform a multipoint internal calibration incorporated into the disclosed method. The data show that the internal calibration produces results with equivalent precision and accuracy as the state-of-the-art 7 point external calibration. The examples of the shown 9 different analytes reveal that the analytical performance according to external calibration and the disclosed method is equivalent. The internal calibration included in the disclosed method reduces the need for calibration standards and their measurement as only a single calibration standard is necessary for sufficient standardization.

It is to be noted that isotope concentrations and abundances, respectively, may be adjusted by mixing two different synthetic internal standards. For example, two different internal standard labels, one of which is deuterated and the other one is a 13C, may be mixed together in different compositions to customize the distribution of the individual isotopes. Thus, isotopic distributions can be tailor made by mixing two different labelled substances together in different compositions. Therefore, it is possible to customize the calibration points of the internal calibration to desired concentrations.

LIST OF REFERENCE NUMBERS

100 apparatus
102 sample

104 mass spectrometer
106 control unit
108 standard solution
110 sample function curve
112 standardization function
114 graph

The invention claimed is:

1. A method for determining a concentration of a target analyte in a sample of bodily fluid, comprising:

providing the sample of bodily fluid, providing an internal standard solution including a mixture of components comprising a plurality of isotopes of the target analyte, wherein a concentration of each isotope is unknown, adding the internal standard solution, wherein the concentration of each isotope is unknown, to the sample of bodily fluid to create a working solution, analyzing the working solution by means of a mass spectrometer to identify a plurality of signal intensities associated with the concentration of each isotope of the working solution, creating a sample function curve based on the plurality of signal intensities, wherein the signal intensities define arbitrary units, transferring an analyte signal into a corresponding arbitrary analyte unit by means of the sample function curve, and transferring the arbitrary analyte unit into the concentration of the target analyte in the sample of bodily fluid by means of a standardization function representing a curve of concentrations depending on the arbitrary units.

2. The method of claim 1, wherein the standardization function is created by analyzing patient samples, wherein each of the patient samples comprises a known concentration of the target analyte.

3. The method of claim 2, wherein the patient samples are mixed with the internal standard solution.

4. The method of claim 1, wherein the sample of bodily fluid is provided with a predetermined volume, wherein the internal standard solution is added to the sample of bodily fluid with a predetermined volume.

5. The method of claim 1, wherein the components are ranked according to the signal intensities.

6. The method of claim 5, wherein the components are ranked from high intensity to low intensity.

7. The method of claim 1, wherein the sample function curve is created based on plotting the signal intensities depending on the arbitrary units.

8. The method of claim 7, wherein the sample function curve is created by calculation from the plotted signal intensities.

9. The method of claim 1, wherein the standardization function is a polynomial function, an exponential function or partial linear function.

10. The method of claim 1, wherein the patient samples are measured according to a reference method.

11. The method of claim 1, wherein the standardization function depends on the type of target analyte.

12. The method of claim 1, wherein the plurality of isotopes are stable isotopes.

13. The method of claim 1, wherein the sample of bodily fluid and the added internal standard solution are analyzed in a single measurement by means of the mass spectrometer.

14. An apparatus for determining a concentration of a target analyte in a sample of bodily fluid, comprising a mass spectrometer and a control unit configured to carry out the method according to claim 1.

15. A method for determining a concentration of a target analyte in a sample of bodily fluid, comprising:

providing a plurality of patient samples, wherein each of the patient samples comprises a known concentration of the target analyte;

providing an internal standard solution including a mixture of a plurality of isotopes of the target analyte, wherein a concentration of each isotope is unknown;

adding the internal standard solution, wherein the concentration of each isotope is unknown, to the plurality of patient samples to create a plurality of spiked samples;

analyzing the plurality of spiked samples by means of a mass spectrometer to identify a first plurality of signal intensities associated with the concentration of each isotope of the plurality of spiked samples;

associating the first plurality of signal intensities with a plurality of arbitrary units that express a relation among the first plurality of signal intensities;

using the first plurality of signal intensities and the plurality of arbitrary units to create a standardization function representing a curve of concentrations depending on the plurality of arbitrary units;

adding the internal standard solution, wherein the concentration of each isotope is unknown, to the sample of bodily fluid to create a working solution, wherein the concentration of the target analyte in the sample of bodily fluid is to be determined;

analyzing the working solution by means of the mass spectrometer to identify a second plurality of signal intensities associated with the concentration of each isotope of the working solution and an analyte signal associated with the sample of bodily fluid;

creating a sample function curve based on the second plurality of signal intensities and the plurality of arbitrary units;

using the sample function curve to determine an arbitrary analyte unit corresponding to the analyte signal; and using the standardization function to determine a value corresponding to the arbitrary analyte unit, wherein the value is representative of the concentration of the target analyte in the sample of bodily fluid.

* * * * *